(12) United States Patent
Tanagi et al.

(10) Patent No.: US 10,472,343 B2
(45) Date of Patent: Nov. 12, 2019

(54) METHOD FOR PRODUCING 1,2,3,5,6-PENTATHIEPANE

(71) Applicant: MITSUBISHI GAS CHEMICAL COMPANY, INC., Tokyo (JP)

(72) Inventors: Hiroyuki Tanagi, Tokyo (JP); Yoshiaki Yamamoto, Tokyo (JP); Hiroshi Horikoshi, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 16/073,609

(22) PCT Filed: Jan. 15, 2018

(86) PCT No.: PCT/JP2018/000737
§ 371 (c)(1),
(2) Date: Jul. 27, 2018

(87) PCT Pub. No.: WO2018/135417
PCT Pub. Date: Jul. 26, 2018

(65) Prior Publication Data
US 2019/0040035 A1 Feb. 7, 2019

(30) Foreign Application Priority Data

Jan. 23, 2017 (JP) ................................. 2017-009257

(51) Int. Cl.
*C07D 341/00* (2006.01)
(52) U.S. Cl.
CPC ................. *C07D 341/00* (2013.01)
(58) Field of Classification Search
CPC .................................................. C07D 341/00
USPC .......................................................... 549/11
See application file for complete search history.

(56) References Cited

U.S. PATENT DOCUMENTS

| 3,503,758 A | 3/1970 | Wada et al. |
| 2002/0107338 A1 | 8/2002 | Wonmun et al. |
| 2005/0199854 A1 | 9/2005 | Wonmun et al. |

FOREIGN PATENT DOCUMENTS

| CN | 101897419 A | 12/2010 |
| CN | 101914087 A | 12/2010 |
| CN | 102260240 A | 11/2011 |
| JP | 2002-040201 A | 2/2002 |
| JP | 2002-293783 A | 10/2002 |
| JP | 4573148 B2 | 11/2010 |
| JP | 2017-165950 A | 9/2017 |
| WO | 2005/034974 A1 | 4/2005 |

OTHER PUBLICATIONS

Liu, Jingxi Shiyou Huagong (2005), (1), 21-22.*
Hansen Tetrahedron 41(22), 5145-5148, 1995.*
Foli, European Symposium on Computer-Aided Process Engineering—14 A. Barbosa-Póvoa and H. Matos (Editors), 2004.*
Liu et al., "Improvement of Synthesis of lenthionine", Speciality Petrochemicals, 2005, pp. 21-22.
Still et al., "A Simple, Efficient Synthesis of Lenthionine and 1, 2, 4, 6-Tetrathiepane from Dimethyl Disulfide", Tetrahedron Letters, vol. 22, No. 21, 1981, pp. 1939-1940.
Hansen et al., "Synthesis, Structure, and Reactions of Thiocarbonic Acid Derivatives New Pentathiodipercarbonates", Tetrahedron, vol. 41, No. 22, 1985, pp. 5145-5158.
Liu et al., "Synthesis and thermal analysis of lenthionine", China Condiment, No. 9, 2005, pp. 25-27.
International Search Report on Patentability issued with respect to Patent Application No. PCT/JP2018/000737, dated Mar. 13, 2018.
European Search Report issued with respect to Application No. 18741370.3, dated Nov. 27, 2018.
G. Gattow et al., Z. Anorg. Allg. Chem., vol. 345 (1966) pp. 137-150
Liu Hong-xia et al., "Review of sulfur-containing heterocyclic perfumes", China Condiment, No. 7, Jul. 2018, pp. 20-24.
"1,2,3,5,6-Pentathiepane", Science and Technology of Food Industry, vol. 25, No. 7, 2004, pp. 117-118.

* cited by examiner

*Primary Examiner* — Nizal S Chandrakumar
(74) *Attorney, Agent, or Firm* — Greenblum & Bernstein, P.L.C.

(57) ABSTRACT

The present invention can provide a method for producing 1,2,3,5,6-pentathiepane, comprising Steps A and B:
Step A: a step of synthesizing a tetrathiocarbonate in a protic solvent; and
Step B: a step of carrying out reaction between the tetrathiocarbonate and a dihalogenated methane in a mixed solvent (where the mass ratio of a protic solvent and an aprotic solvent is 13:87-38:62).

2 Claims, No Drawings

METHOD FOR PRODUCING 1,2,3,5,6-PENTATHIEPANE

TECHNICAL FIELD

The present invention relates to a method for producing highly pure 1,2,3,5,6-pentathiepane.

BACKGROUND ART 1,2,3,5,6-Pentathiepane (hereinafter, sometimes referred to as "lenthionine") is a compound useful for optical material applications (Patent document 1) and medical applications (Patent document 2), which is expected to be used for a wide range of applications.

As a method for synthesizing lenthionine, for example, a method that uses dimethyl disulfide as a starting raw material is known (Non-patent document 1). According to this method, the reaction results an oily solution that contains lenthionine and thus it needs to be purified by column chromatography, which is industrially disadvantageous. Moreover, dimethyl disulfide that is uneasy to obtain for industrial application needs to be used as the raw material.

Meanwhile, a method is known in which sodium sulfide as a starting raw material is allowed to react with diiodomethane or dibromomethane in an ethanol solvent (Non-patent document 2). This method also requires column chromatography for purification, which is industrially disadvantageous.

In general, disulfide and trisulfide are known to be susceptible to linkage and cleavage. Since lenthionine has disulfide and trisulfide bonds, polymerization proceeds when these bonds are cleaved, resulting an insoluble polysulfide compound.

Generation of a large amount of the insoluble polysulfide compound in the reaction system not only makes washing and industrialization difficult, but eventually makes acquirement of highly pure lenthionine difficult due to contamination in the final lenthionine. Generation of this polysulfide is making purification in the known lenthionine syntheses difficult.

PRIOR ART DOCUMENTS

Patent Documents

Patent document 1: Japanese Patent No. 4573148
Patent document 2: WO2005/034974

Non-Patent Documents

Non-patent document 1: Tetrahedron. lett_1981_22_1939
Non-patent document 2: SPECIALTY PETROCHEMICALS 2005 p22

SUMMARY OF THE INVENTION

Problems to be Solved by the Invention

The objective of the present invention is to provide a method for producing highly pure lenthionine in a simple manner while suppressing generation of an insoluble polysulfide compound.

Means for Solving the Problems

The present inventors have gone through keen studies, and as a result of which found that the above-described problem can be solved by carrying out reaction between a tetrathiocarbonate and a dihalogenated methane in a specific solvent.

Thus, the present invention is as follows.

[1] A method for producing 1,2,3,5,6-pentathiepane, comprising Steps A and B:
Step A: a step of synthesizing a tetrathiocarbonate in a protic solvent; and
Step B: a step of carrying out reaction between the tetrathiocarbonate and a dihalogenated methane in a mixed solvent (where the mass ratio of a protic solvent and an aprotic solvent is 13:87-38:62).
[2] The method for producing 1,2,3,5,6-pentathiepane according to [1], wherein the protic solvent comprises an alcohol.
[3] The method for producing 1,2,3,5,6-pentathiepane according to [1], wherein the protic solvent comprises ethanol.
[4] The method for producing 1,2,3,5,6-pentathiepane according to any one of [1]-[3], wherein the aprotic solvent comprises an aromatic hydrocarbon.
[5] The method for producing 1,2,3,5,6-pentathiepane according to any one of [1]-[3], wherein the aprotic solvent comprises toluene.
[6] The method for producing 1,2,3,5,6-pentathiepane according to any one of [1]-[5], wherein the tetrathiocarbonate is sodium tetrathiocarbonate.
[7] The method for producing 1,2,3,5,6-pentathiepane according to any one of [1]-[6], wherein the dihalogenated methane comprises dibromomethane or diiodomethane.
[8] The method for producing 1,2,3,5,6-pentathiepane according to any one of [1]-[7], wherein Steps A and B are carried out sequentially.

Advantageous Effect of the Invention

According to the present invention, highly pure lenthionine can be produced in a simple manner while suppressing generation of an insoluble polysulfide compound. This highly pure lenthionine can favorably be used for various applications like enhancing performance of an optical material.

EMBODIMENTS FOR CARRYING OUT THE INVENTION

A method for producing lenthionine according to the present invention has the following Steps A and B:
Step A: a step of synthesizing a tetrathiocarbonate in a protic solvent; and
Step B: a step of carrying out reaction between the tetrathiocarbonate and a dihalogenated methane in a mixed solvent (where the mass ratio of a protic solvent and an aprotic solvent is 13:87-38:62).

Hereinafter, these Steps A and B will be described in detail.

<Regarding Step A: Step of Synthesizing Tetrathiocarbonate in Protic Solvent>

[Tetrathiocarbonate]

The tetrathiocarbonate used with the present invention is a compound represented by $M_2CS_4$ (where M represents cation species). Specific examples of a preferable tetrathiocarbonate include sodium tetrathiocarbonate, potassium tetrathiocarbonate and lithium tetrathiocarbonate, where sodium tetrathiocarbonate represented by the following structural formula is more preferable since its raw materials can easily be obtained for industrial application and it can be synthesized in a simple manner.

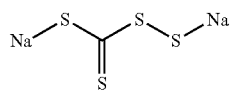

[Protic Solvent]

Any protic solvent can be used in Step A as long as it is a solvent that can be mixed with the aprotic solvent used in Step B.

Specific examples include water, methanol, ethanol, n-propanol, isopropanol, n-butanol, isobutanol, t-butanol, n-pentanol, neopentanol, n-hexanol, n-heptanol, n-octanol, n-nonanol, n-decanol, ethylene glycol and propylene glycol, where methanol, ethanol and isopropanol are preferable due to high solubility with the later-described sulfide salt, and ethanol is particularly preferable. Two or more of them can be used in combination.

The amount of the protic solvent used in Step A is preferably in a range of 5-40 mass times that of the sulfide salt, and more preferably in a range of 10-30 mass times for the sake of production efficiency and reactivity.

[Method for Synthesizing Tetrathiocarbonate]

The tetrathiocarbonate can be obtained by reacting a sulfide salt, carbon disulfide and sulfur in the protic solvent. Specific examples of the sulfide salt include sodium sulfide, potassium sulfide and lithium sulfide.

For example, sodium tetrathiocarbonate can easily be synthesized by reacting sodium sulfide and carbon disulfide in an ethanol to synthesize sodium trithiocarbonate, and adding sulfur to the resultant.

The amount of carbon disulfide used is preferably in a range of 0.5-1.5 molar equivalent to the sulfide salt, and more preferably in a range of 0.8-1.2 molar equivalent to be able to suppress progress of the side reaction.

The amount of sulfur used is preferably in a range of 0.5-1.5 molar equivalent to the sulfide salt, and more preferably in a range of 0.8-1.2 molar equivalent to be able to suppress progress of the side reaction.

The reaction temperature is in a range of −10-60° C., and preferably in a range of 20-40° C. for the sake of the reaction time and the reaction yield.

<Regarding Step B: Step of Carrying Out Reaction Between Tetrathiocarbonate and Dihalogenated Methane in Mixed Solvent (Where Mass Ratio of Protic Solvent and Aprotic Solvent is 13:87-38:62)>

[Tetrathiocarbonate]

The tetrathiocarbonate in Step B is the one obtained in Step A, and the reaction solution from Step A can directly and sequentially be used.

[Dihalogenated Methane]

The dihalogenated methane used with the present invention refers to dichloromethane, dibromomethane, diiodomethane, chlorobromomethane, chloroiodomethane or bromoiodomethane, which is preferably dibromomethane and diiodomethane in terms of reactivity, and particularly preferably dibromomethane.

The amount of the dihalogenated methane used is preferably in a range of 0.5-1.5 molar equivalent to the tetrathiocarbonate, and more preferably in a range of 0.8-1.2 molar equivalent to be able to suppress progress of the side reaction.

[Protic Solvent]

The protic solvent in Step B can be selected from the protic solvents that can be used in Step A. Alternatively, the protic solvent of Step A can directly be used to sequentially conduct the reaction.

The amount of the protic solvent used in Step B is preferably in a range of 5-40 mass times that of the tetrathiocarbonate, and more preferably in a range of 10-30 mass times for the sake of production efficiency and reactivity.

[Aprotic Solvent]

Examples of the aprotic solvent includes hydrocarbon-, aromatic hydrocarbon-, ether-, ester-, nitrile-, ketone-, amide- and halogen-based solvents. Among them, hydrocarbon, aromatic hydrocarbon and ether solvents are preferable due to high lanthionine reaction yield and easy solvent removal after the reaction. It is more preferably a cyclic compound, particularly preferably benzene, toluene or tetrahydrofuran, and most preferably toluene in terms of yield. Two or more of them may be used in combination.

[Reaction Between Tetrathiocarbonate and Dihalogenated Methane]

The reaction between the tetrathiocarbonate and the dihalogenated methane is carried out in a mixed solvent of the protic solvent and the aprotic solvent. The mass ratio of the protic solvent and the aprotic solvent is 13:87-38:62, and preferably 15:85-30:70. If the amount of the protic solvent is too much, an insoluble polysulfide compound will be generated whereas if the amount of the aprotic solvent is too much, the reaction does not proceed.

The amount of the mixed solvent used is preferably in a range of 5-40 mass that of the tetrathiocarbonate, and more preferably 10-30 mass times for the sake of production efficiency and reactivity.

The temperature of the reaction between the tetrathiocarbonate and the dihalogenated methane is preferably in a range of −10-60° C., and more preferably in a range of 20-40° C. Too low temperature will delay the reaction whereas too high temperature is likely to progress side reaction.

An aqueous acid solution is added after the reaction between the tetrathiocarbonate and the dihalogenated methane to quench the reaction. While any aqueous acid solution can be used as long as it is an aqueous acidic solution, industrially inexpensive sulfuric acid, hydrochloric acid, nitric acid and phosphoric acid can favorably be used.

In addition, purification can be conducted after the quenching. The present invention is favorable since highly pure lenthionine can easily be acquired by a crystallization process while generation of an insoluble polysulfide compound is hardly confirmed in the reaction system.

EXAMPLES

Hereinafter, the present invention will specifically be described by way of examples. The embodiments can suitably be modified as long as the effect of the present invention can be achieved.

[Method for Analyzing Lenthionine]

The analysis was carried out by using a liquid chromatograph and an ODS column (column; VP-ODS, column size 4.6φ×150 mm, from CERT).

An RI detector was used to calculate the lenthionine generation yield based on the molar ratio of methylene bromide as a raw material.

[Conditions for Liquid Chromatograph]

Oven temperature: 40° C.

Eluent: acetonitrile/distilled water (volume ratio)=50/50

Solution preparation: 5 mg of a sample was diluted with 10 ml of a 0.1% formic acid solution (acetonitrile solvent) to give an analysis sample.

[Method for Measuring Amount of Insoluble Polysulfide Compound]

While lenthionine is readily soluble in toluene, polysulfide compounds are insoluble in toluene. Accordingly, the solid in the system confirmed after the quenching was collected by filtration, to which 50 ml of toluene was added. The resultant was further washed with water, and the insoluble matter in toluene was collected by filtration and dried for mass measurement.

Example 1

[Solvent: Ethanol:Toluene=26.4:73.6]

5.9 g (76 mmol) of sodium sulfide was dissolved in 120 g of ethanol, to which 5.8 g (76 mmol) of carbon disulfide was added to allow reaction at 35° C. for 20 minutes. 2.4 g (76 mmol) of sulfur was added to the resulting reaction solution to allow additional reaction at 35° C. for an hour, thereby preparing an ethanol solution of sodium tetrathiocarbonate.

Next, 334 g of toluene was added to dilute 13.2 g (76 mmol) of dibromomethane. The previously prepared ethanol solution of sodium tetrathiocarbonate was dropped into the toluene solution of dibromomethane to allow reaction at 35° C.

The yield of lenthionine generation was 33 mol % after 3 hours, and 43 mol % after 20 hours. After 20 hours, 100 g of a 1N aqueous sulfuric acid solution was added for quenching. This process gave two separate layers, namely, an aqueous layer and an organic layer. The organic layer was washed three times with 100 ml of ion-exchanged water. No polysulfide compound was confirmed in any of the steps.

Example 2

[Solvent: Ethanol:Toluene 26.5:73.5]

30 g of ethanol was added to 5.9 g (76 mmol) of sodium sulfide, into which 5.8 g (76 mmol) of carbon disulfide was dropped to allow reaction at 35° C. for an hour. 2.4 g (76 mmol) of sulfur was added to the resulting reaction solution to allow additional reaction at 35° C. for an hour. 83 g of toluene was added to the resulting yellow slurry solution, into which 13.2 g (76 mmol) of dibromomethane was dropped to allow reaction at 35° C.

The yield of lenthionine generation was 46 mol % after 3 hours, and 45 mol % after 20 hours. After 20 hours, the same process as Example 1 was conducted. No polysulfide compound was confirmed in any of the steps.

Example 3

[Solvent: Ethanol:Toluene=13.2:86.8]

Reaction was carried out under the same conditions as those in Example 2 except that the solvents used was 15 g of ethanol and 99 g of toluene.

The yield of lenthionine generation was 10 mol % after 3 hours, and 30 mol % after 20 hours. No polysulfide compound was confirmed in any of the steps.

Example 4

[Solvent: Methanol:Toluene=26.4:73.6]

Reaction was carried out under the same conditions as those in Example 1 except that the solvents used was 120 g of methanol and 334 g of toluene.

The yield of lenthionine generation was 34 mol % after 3 hours, and 30 mol % after 20 hours. No polysulfide compound was confirmed in any of the steps.

Example 5

[Solvent: Ethanol:Toluene=35.4:64.6]

40 g of ethanol was added to 5.9 g (76 mmol) of sodium sulfide, into which 5.8 g (76 mmol) of carbon disulfide was dropped to allow reaction at 35° C. for an hour. 2.4 g (76 mmol) of sulfur was added to the resulting reaction solution to allow additional reaction at 35° C. for an hour. 73 g of toluene was added to the resulting yellow slurry solution, into which 13.2 g (76 mmol) of dibromomethane was dropped to allow reaction at 35° C.

The yield of lenthionine generation was 43 mol % after 3 hours, and 40 mol % after 20 hours. After 20 hours, the same process as Example 1 was conducted. No polysulfide compound was confirmed in any of the steps.

Example 6

[Solvent: Ethanol:Toluene=26.7:73.3]

455 g of ethanol was added to 90 g (1.15 mol) of sodium sulfide and agitated at 30° C. for an hour. 87.9 g (1.15 mol) of carbon disulfide was further added to allow reaction at 35° C. for an hour. 36.7 g (1.14 mol) of sulfur was added to the resulting reaction solution to allow additional reaction at 35° C. for an hour. 1250 g of toluene was added to the resulting yellow slurry solution, into which 198 g (1.15 mmol) of dibromomethane was dropped to allow reaction at 35° C. for 20 hours.

The yield of lenthionine generation was 40 mol % after 3 hours, and 43 mol % after 20 hours. After 20 hours, 750 g of a 1N aqueous sulfuric acid solution was added for quenching and the aqueous layer was removed. The resultant was further washed twice with 350 ml of ion-exchanged water. The toluene layer was separated and the resultant was concentrated to 100 ml with an evaporator under the conditions of 30-40 torr and 40° C. The resultant was cooled to 0 to −1° C. while agitating to perform a crystallization process. The resulting solid was filtered and dried to acquire 31.9 g of lenthionine with a purity of 99% (isolation yield 29.4 mol %). No polysulfide compound was confirmed in any of the steps.

Comparative Example 1

[Solvent: 100% Ethanol Condition]

Lenthionine was synthesized according to a Chinese document (CHINA CONDIMENT, September, 2005, No. 9, p 25).

Specifically, 5.9 g (76 mmol) of sodium sulfide was dissolved in 67 g of ethanol, to which 5.8 g (76 mmol) of carbon disulfide was added to allow reaction at 35° C. for 20 minutes. 2.4 g (76 mmol) of sulfur was added to the resulting reaction solution to allow additional reaction at 35° C. for an hour, thereby preparing an ethanol solution of sodium tetrathiocarbonate.

18 g of ethanol was added to dilute 13.2 g (76 mmol) of dibromomethane. The ethanol solution of dibromomethane was dropped into the previously prepared ethanol solution of sodium tetrathiocarbonate to allow reaction at 35° C.

The yield of lenthionine generation was 5 mol % after 3 hours, and 4 mol % after 20 hours. After 20 hours, 100 g of a 1N aqueous sulfuric acid solution was added for quenching, and the resultant was washed three times with 100 ml of ion-exchanged water. The residue was a yellow oily compound. When 100 g of toluene was added, a large amount of insoluble component was generated, whose mass was measured 2.1 g. IR measurement confirmed that it was a polysulfide compound.

When a crystallization process was conducted in the same manner as Example 6, the crude crystal contained a polysulfide compound, meaning that crystallization did not give a high purity product.

Comparative Example 2

[Solvent: 100% Ethanol Condition]

5.9 g (76 mmol) of sodium sulfide was dissolved in 120 g of ethanol, and the resultant was added with 5.8 g (76 mmol) of carbon disulfide to allow reaction at 35° C. for 20 minutes. 2.4 g (76 mmol) of sulfur was added to the resulting reaction solution to allow additional reaction at 35° C. for an hour, thereby preparing an ethanol solution of sodium tetrathiocarbonate.

302 g of ethanol was added to dilute 13.2 g (76 mmol) of dibromomethane. The previously prepared ethanol solution of sodium tetrathiocarbonate was dropped into an ethanol solution of dibromomethane to allow reaction at 35° C. As a result, the yield of lenthionine generation was 23 mol % after 3 hours, and 23 mol % after 20 hours. After 20 hours, 100 g of a 1N aqueous sulfuric acid solution was added for quenching, 100 g of toluene was added for extraction, and the resultant was washed three times with 100 ml of ion-exchanged water.

The toluene solution was concentrated to 12 g and then a crystallization process was conducted in the same manner as Example 6. As a result, 1.1 g of crude crystal (purity 95%) was obtained but it contained 2.3 g of a polysulfide compound, meaning that crystallization did not give a high purity product.

Comparative Example 3

[Solvent: 100% Methanol Condition]

The same process as Comparative example 2 was conducted except that the solvent used was changed from ethanol to methanol. The yield of lenthionine generation was 17 mol % after 3 hours, and 9 mol % after 20 hours. When a crystallization process was conducted in the same manner as Example 6, the crude crystal contained a polysulfide compound, meaning that crystallization did not give a high purity product. The polysulfide compound was 1.6 g.

Comparative Example 4

[Solvent: 100% Toluene Condition]

An ethanol solution of sodium tetrathiocarbonate was prepared in the same manner as Comparative example 2, where ethanol, i.e., the solvent, was removed with an evaporator. 120 g of toluene was added to prepare a suspension of sodium tetrathiocarbonate. 13.2 g (76 mmol) of dibromomethane was diluted with 334 g of toluene, and the resultant was added to the toluene solution of sodium tetrathiocarbonate to allow reaction at 35° C. No lenthionine generation was confirmed after 3 and 20 hours. Supposedly, the reaction did not proceed because sodium tetrathiocarbonate was insoluble toluene.

Comparative Example 5

[Solvent: Ethanol:Toluene=67.4:32.6]

5.9 g (76 mmol) of sodium sulfide was dissolved in 87 g of ethanol, to which 5.8 g (76 mmol) of carbon disulfide was added to allow reaction at 35° C. for an hour. 2.4 g (76 mmol) of sulfur was added to the resulting reaction solution to allow additional reaction at 35° C. for an hour. 42 g of toluene was added to this solution, into which 13.2 g (76 mmol) of dibromomethane was dropped to allow reaction at 35° C. The yield of lenthionine generation was 19 mol % after 3 hours, and 13 mol % after 20 hours. A crystallization process was conducted in the same manner as Example 6. As a result, the crude crystal contained a polysulfide compound, meaning that crystallization did not give a high purity product. The polysulfide compound was 4.0 g.

Comparative Example 6

[Solvent: Ethanol:Toluene=50:50]

5.9 g (76 mmol) of sodium sulfide was dissolved in 57 g of ethanol, to which 5.8 g (76 mmol) of carbon disulfide was added to allow reaction at 35° C. for an hour. 2.4 g (76 mmol) of sulfur was added to the resulting reaction solution to allow additional reaction at 35° C. for an hour. 57 g of toluene was added to this solution, into which 13.2 g (76 mmol) of dibromomethane was dropped to allow reaction at 35° C. The yield of lenthionine generation was 33 mol % after 3 hours, and 22 mol % after 20 hours. A crystallization process was conducted in the same manner as Example 6. As a result, the crude crystal contained a polysulfide compound, meaning that crystallization did not give a high purity product. The polysulfide compound was 2.8 g.

Comparative Example 7

[Solvent: Ethanol:Toluene=40:60]

5.9 g (76 mmol) of sodium sulfide was dissolved in 48 g of ethanol, to which 5.8 g (76 mmol) of carbon disulfide was added to allow reaction at 35° C. for an hour. 2.4 g (76 mmol) of sulfur was added to the resulting reaction solution to allow additional reaction at 35° C. for an hour. 72 g of toluene was added to this solution, into which 13.2 g (76 mmol) of dibromomethane was dropped to allow reaction at 35° C. The yield of lenthionine generation was 41 mol % after 3 hours, and 33 mol % after 20 hours. A crystallization process was conducted in the same manner as Example 6. As a result, the crude crystal contained a polysulfide compound, meaning that crystallization did not give a high purity product. The polysulfide compound was 0.5 g.

Comparative Example 8

[Solvent: Ethanol:Toluene=6:94]

7 g of ethanol was added to 5.9 g (76 mmol) of sodium sulfide, into which 5.8 g (76 mmol) of carbon disulfide was dropped to allow reaction at 35° C. for an hour. 2.4 g (76 mmol) of sulfur was added to the resulting reaction solution to allow additional reaction at 35° C. for an hour. 109 g of toluene was added to the yellow slurry solution resulting from the reaction, into which 13.2 g (76 mmol) of dibromomethane was dropped to allow reaction at 35° C. The yield of lenthionine was 5 mol % after 3 hours, and 15 mol % after 20 hours. After 20 hours, the same process as Comparative example 1 was conducted, by which no polysulfide compound that was insoluble in toluene was confirmed. A crystallization process was conducted in the same manner as Example 6 but crystallization did not give a high purity product due to low yield.

TABLE 1

|  |  |  | Example 1 | Example 2 | Example 3 | Example 4 | Example 5 | Example 6 |
|---|---|---|---|---|---|---|---|---|
| Raw material | $Na_2S$ | g | 5.9 | ← | ← | 5.9 | 5.9 | 90 |
|  | $CS_2$ | g | 5.8 | ← | ← | 5.8 | 5.8 | 87.9 |
|  | $S_8$ | g | 2.4 | ← | ← | 2.4 | 2.4 | 36.7 |
|  | $CH_2Br_2$ | g | 13.2 | ← | ← | 13.2 | 13.2 | 198 |
| Protic solvent | EtOH | g | 120 | 30 | 15 |  | 40 | 455 |
|  | MeOH | g |  |  |  | 120 |  |  |
| Aprotic solvent | Toluene | g | 334 | 83 | 99 | 334 | 73 | 1250 |
| Solvent ratio | Protic solvent |  | 26.4 | 26.5 | 13.2 | 26.4 | 35.4 | 26.7 |
|  | Aprotic solvent |  | 73.6 | 73.5 | 86.8 | 73.6 | 64.6 | 73.3 |
| Lenthionine generation | After 3 hours | mol % | 33 | 46 | 10 | 34 | 43 | 40 |
| yield | After 20 hours | mol % | 43 | 45 | 30 | 30 | 40 | 43 |
|  | Polysulfide compound | g | 0 | 0 | 0 | 0 | 0 | 0 |

TABLE 2

|  |  |  | Comparative example 1 | Comparative example 2 | Comparative example 3 | Comparative example 4 | Comparative example 5 | Comparative example 6 | Comparative example 7 | Comparative example 8 |
|---|---|---|---|---|---|---|---|---|---|---|
| Raw material | $Na_2S$ | g | 5.9 | ← | ← | ← | ← | ← | ← | ← |
|  | $CS_2$ | g | 5.8 | ← | ← | ← | ← | ← | ← | ← |
|  | $S_8$ | g | 2.4 | ← | ← | ← | ← | ← | ← | ← |
|  | $CH_2Br_2$ | g | 13.2 | ← | ← | ← | ← | ← | ← | ← |
| Protic solvent | EtOH | g | 85 | 422 |  |  | 87 | 57 | 48 | 7 |
|  | MeOH | g |  |  | 422 |  |  |  |  |  |
| Aprotic solvent | Toluene | g |  |  |  | 454 | 42 | 57 | 72 | 109 |
| Solvent ratio | Protic solvent |  | 100 | 100 | 100 | 0 | 67.4 | 50 | 40 | 6 |
|  | Aprotic solvent |  | 0 | 0 | 0 | 100 | 32.6 | 50 | 60 | 94 |
| Lenthionine generation | After 3 hours | mol % | 5 | 23 | 17 | 0 | 19 | 33 | 41 | 5 |
| yield | After 20 hours | mol % | 4 | 23 | 9 | 0 | 13 | 22 | 33 | 15 |
|  | Polysulfide compound | g | 2.1 | 2.3 | 1.6 | 0 | 4.0 | 2.8 | 0.5 | 0 |

The invention claimed is:

1. A method for producing 1,2,3,5,6-pentathiepane, comprising:

synthesizing a tetrathiocarbonate in a protic solvent; and
carrying out reaction between the tetrathiocarbonate and a dihalogenated methane in a mixture of the protic solvent and an aprotic solvent in which the mass ratio of the protic solvent to the aprotic solvent is 13:87-38:62,
wherein the tetrathiocarbonate is selected from the group consisting of sodium tetrathiocarbonate, potassium tetrathiocarbonate, and lithium tetrathiocarbonate;
wherein the dihalogenated methane comprises dibromomethane or diiodomethane; and
wherein the protic solvent comprises ethanol, methanol, or combinations thereof, and the aprotic solvent is toluene.

2. The method for producing 1,2,3,5,6-pentathiepane according to claim 1, wherein the synthesizing and carrying out reaction are carried out sequentially.

* * * * *